(12) United States Patent
Park et al.

(10) Patent No.: US 10,143,659 B2
(45) Date of Patent: Dec. 4, 2018

(54) MELT-EXTRUDED RELEASE CONTROLLED PHARMACEUTICAL COMPOSITION AND ORAL DOSAGE FORM COMPRISING THE SAME

(71) Applicant: Samyang Biopharmaceuticals Corporation, Seoul (KR)

(72) Inventors: Sang-Yeob Park, Daejeon (KR); Hye-Jung Lim, Daejeon (KR); Kyung-Hee Kim, Daejeon (KR)

(73) Assignee: Samyang Biopharmaceutical Corporation, Seoul (KR)

( * ) Notice: Subject to any disclaimer, the term of this patent is extended or adjusted under 35 U.S.C. 154(b) by 2 days.

(21) Appl. No.: 14/758,258

(22) PCT Filed: Dec. 20, 2013

(86) PCT No.: PCT/KR2013/011972
§ 371 (c)(1),
(2) Date: Jun. 29, 2015

(87) PCT Pub. No.: WO2014/104670
PCT Pub. Date: Jul. 3, 2014

(65) Prior Publication Data
US 2016/0213621 A1 Jul. 28, 2016

(30) Foreign Application Priority Data
Dec. 31, 2012 (KR) ........................ 10-2012-0158570

(51) Int. Cl.
| A61K 9/50 | (2006.01) |
| A61K 31/519 | (2006.01) |
| A61K 47/32 | (2006.01) |
| A61K 31/517 | (2006.01) |
| A61K 9/16 | (2006.01) |

(52) U.S. Cl.
CPC .......... *A61K 9/5026* (2013.01); *A61K 31/517* (2013.01); *A61K 31/519* (2013.01); *A61K 47/32* (2013.01); *A61K 9/1635* (2013.01)

(58) Field of Classification Search
None
See application file for complete search history.

(56) References Cited

U.S. PATENT DOCUMENTS

| 6,488,963 B1 | 12/2002 | McGinity et al. | |
| 2009/0011007 A1* | 1/2009 | Meier | A61K 9/1635 424/451 |
| 2009/0148517 A1* | 6/2009 | Oshlack | A61K 9/1617 424/456 |
| 2009/0317355 A1 | 12/2009 | Roth et al. | |
| 2010/0086589 A1 | 4/2010 | Friedl et al. | |
| 2012/0141583 A1 | 6/2012 | Mannion et al. | |

FOREIGN PATENT DOCUMENTS

| JP | H06-501685 A | 2/1994 | |
| JP | H10-508608 A | 8/1998 | |
| JP | 2001031591 A | 2/2001 | |
| JP | 2007510677 A | 4/2007 | |
| JP | 2008540541 A | 11/2008 | |
| JP | 2012176993 A | 9/2012 | |
| KR | 10-2002-0024714 | 4/2002 | |
| KR | 10-2007-0029673 | 3/2007 | |
| KR | 10-2007-0118444 | 12/2007 | |
| KR | 10-1189038 | 9/2012 | |
| WO | WO-96/14058 A1 | 5/1996 | |
| WO | WO-2010/009900 A1 | 1/2010 | |
| WO | WO-2010026467 A2 * | 3/2010 | ........... A61K 9/2027 |

OTHER PUBLICATIONS

Giri et al., "A Novel and Alternative Approach to Controlled Release Drug Delivery System Based on Solid Dispersion Technique", Bulletin of Faculty of Pharmacy, Cairo University (2012) 50, pp. 147-159.
Islam et al., "Preparation and Characterization of Polyvinyl Acetate (Kollidon® SR) Microspheres Containing Diclofenac Sodium: Effect of Different Cellulosic and Acrylic Polymers", International Journal of Pharma and Bio Sciences V1(2) 2010, 13 pages.
Zhang et al., Drug Development Industrial Pharmacy, vol. 26, No. 9, pp. 931-942, 2000.
International Search Report and Written Opinion in International Application No. PCT/KR2013/011972 dated Apr. 11, 2014.
Pearnchob et al., "Dry Powder Coating of Pellets with Micronized Eudragit® RS for Extended Drug Release", Pharmaceutical Research, vol. 20, No. 12, Dec. 2003, pp. 1970-1976.
Extended European Search Report in EP Application No. 13869605.9 dated Aug. 19, 2016, 5 pages.

* cited by examiner

Primary Examiner — Bethany P Barham
Assistant Examiner — Dominic Lazaro
(74) Attorney, Agent, or Firm — Marshall, Gerstein & Borun LLP

(57) ABSTRACT

Disclosed are a controlled release pharmaceutical composition, comprising a melt-extruded pellet including a water-insoluble ammonium methacrylate copolymer, a polyvinyl acetate, and an active ingredient; and a polymer coating layer including a water-insoluble ammonium methacrylate copolymer formed on the surface of the pellet, and an oral formulation including the pharmaceutical composition.

16 Claims, No Drawings

MELT-EXTRUDED RELEASE CONTROLLED PHARMACEUTICAL COMPOSITION AND ORAL DOSAGE FORM COMPRISING THE SAME

BACKGROUND OF THE INVENTION (a) Field of the Invention

The present invention provides a controlled release pharmaceutical composition comprising a melt-extruded pellet including a water-insoluble ammonium methacrylate copolymer, a polyvinyl acetate and an active ingredient; and a polymer coating layer including a water-insoluble ammonium methacrylate copolymer formed on the surface of the pellet, and an oral formulation including the pharmaceutical composition.

(b) Description of the Related Art

A controlled release pharmaceutical formulation is advantageous in maintaining the drug efficacy time and reducing the side-effect, by controlling the release of active ingredient to stay the drug blood level at a target region for a long time. In addition, the controlled release pharmaceutical formulation is in the limelight, because it improves the patient's convenience by reducing the number of administration, and because it increases the treatment efficiency by maintaining the suitable blood level and the safety by reducing the side-effect. The controlled release formulation needs for a patient who needs frequent administration, for example, 2 to 4 times a day and has low medication compliance.

In the schizophrenia, the psychotic state mixed with at least one of emotional, behavioral, and mental weakness is lasted continuously or reoccurred and thus needs long-term treatment. Because a patient denies the frequent administration, the controlled release formulation has been developed for oral administration once daily or delayed action injections for a week or a month.

Paliperidone is atypical schizophrenia therapeutic called as 9-hydroxy-risperidone. Janssen has launched paliperidone as an slow-release drug formulation of Osmotic Release Oral delivery System which releases the paliperidone at zero order kinetics by administering once in a day (INVEGA™ extended-release tablet) and paliperidone palmitate as an injections administered one in a month (INVEGA™ Sustenna). Paliperidone is one of active metabolite of risperidone and has an additional hydroxyl group compared to risperidone. Paliperidone has been used for treating acute and chronic schizophrenia. Paliperidone obviates the hepatic drug metabolism, and thus is not seriously affected by dyshepatia, injury of liver, metabolic enzyme, the patient's condition and the like. Paliperidone is poorly soluble in water, and thus is well dissolved in methylene chloride, methanol and 0.1N hydrochloric acid.

Recently, the hot melt extrusion method which was used in the plastic manufacturing process has been introduced to the pharmaceutical industry to increase the bioavailability and to provide the controlled release drug formulation.

U.S. Pat. No. 6,488,963 discloses the preparation of controlled release formulation by extruding an active ingredient and Poly(ethylene oxide) having a high molecular weight of 1,000,000 to 10,000,000 according to the hot melt extrusion method. Although the composition can provide the delayed release formulation with 12 hours or shorter of drug release time, it has difficulty in preparing the delayed release formulation with the drug release time longer than 12 hours.

KR10-1189038 discloses a controlled release formulation including multi-particles produced by the hot melt extrusion method, which includes an active ingredient and a rubber-shape matrix of neutral poly(ethylacrylatemethylmethacrylate) copolymer. All available poly(ethylacrylatemethylmethacrylate) copolymer are sold in an aqueous dispersion and thus needs an additional step such as a wet-granulation disadvantageously.

WO1996/14058 discloses a melt-extruded blend including a drug and one or more hydrophobic materials selected from the group consisting of alkylcellulose, acrylic and methacrylic acid polymers and copolymers, shellac, zein, hydrogenated castor oil, hydrogenated vegetable oil and a mixture thereof.

However, the publications related with the melt-extruded formulation cannot provide the controlled release formulations for various drugs and with a long release time over 12 hours, pH-independent drug release or drug release at zero order kinetics.

Therefore, the controlled release formulation which can control the side-effect of rapid drug release, extend the drug release time, and adjust the drug release pattern to the desired pattern and to close to zero order kinetics without being affected by pH condition, is still needed.

SUMMARY OF THE INVENTION

The present invention is to provide a technology for effectively controlling the release of active ingredient to the desired pattern, by the controlled release pharmaceutical composition comprising a melt-extruded pellet including a water-insoluble ammonium methacrylate copolymer, polyvinyl acetate, and active ingredient; and a polymer coating layer formed on the pellet including a water-insoluble ammonium methacrylate copolymer.

An embodiment of the present invention is to provide a controlled release pharmaceutical composition comprising a melt-extruded pellet including water-insoluble ammonium methacrylate copolymer, polyvinyl acetate, and active ingredient; and a polymer coating layer formed on the pellet including a water-insoluble ammonium methacrylate copolymer Another embodiment of the present invention is to provide an oral formulation including the controlled release pharmaceutical composition.

Further embodiment of the present invention is to provide a method of preparing the oral formulation including the controlled release pharmaceutical composition.

The present invention relates to a controlled release pharmaceutical composition and an oral formulation including the composition with controlling effectively the release of active ingredient to the desired pattern.

Hereinafter, the controlled release pharmaceutical composition and the oral formulation including the composition are described in more detail.

Definition of Terms

Unless specifically defined otherwise, all technical or scientific terms used herein are defined as follows.

Unless specifically defined herein, the term, "comprise" or "include" means that an element and an ingredient can be added without limitation, but shall not be interpreted to exclude other additional elements and ingredients.

The term, "active ingredient" refers to include any drug (base drug itself without the salt), its pharmaceutically acceptable salt, its isomer, and a mixture thereof.

The term, "controlled release" means that the release of any active ingredient may be controlled to the desired pattern and includes the controlled release, slow-release, delayed release, pulse-type release and a combined release type thereof.

Controlled Release Pharmaceutical Composition

In the present invention, the controlled release pharmaceutical composition comprising a melt-extruded pellet comprising water-insoluble ammonium methacrylate copolymer, polyvinyl acetate, and active ingredient; and a polymer coating layer formed on the pellet comprising a water-insoluble ammonium methacrylate copolymer, has some advantages of:

1) effective control for the release of active ingredient as desired, 2) continuous release of an active ingredient to maximum release time of 24 hours, 3) consistent release of an active ingredient at a pH-independent manner, and 4) maintenance of active ingredient release at close to zero order kinetics.

Because the controlled release pharmaceutical composition maintains the effective blood level of active ingredient for a certain time or longer, it can increase the administration convenience and compliance of patient, and the treatment of oral formulation by shielding bitter taste in a mouth for a certain time.

According to an embodiment of the present invention, a controlled release pharmaceutical composition comprising a melt-extruded pellet comprising water-insoluble ammonium methacrylate copolymer, polyvinyl acetate, and active ingredient; and a polymer coating layer formed on the pellet comprising a water-insoluble ammonium methacrylate copolymer, is provided.

In another embodiment, an oral formulation including the controlled release pharmaceutical composition is provided.

Pellet

The pellet includes a water insoluble ammonium methacrylate copolymer, a polyvinyl acetate and an active ingredient.

The water insoluble ammonium methacrylate copolymer can be poly(ethylacrylate/methylmethacrylate/trimethylammonium chloride methacrylate). The water insoluble ammonium methacrylate copolymer can have a molecular weight of 20,000 to 500,000 Da, for example, 50,000 to 300,000 Da, or 100,000 to 200,000 Da.

In an embodiment, the water insoluble ammonium methacrylate copolymer can be poly(ethylacrylate/methylmethacrylate/trimethylammonium chloride methacrylate) where the moisture-penetrating property can be various, as it depends on the unit of trimethylammonium chloride methacrylate. For example, the water insoluble ammonium methacrylate copolymer can be the polymer including the unit of trimethylammonium chloride methacrylate at an amount of 8.0 to 15.0 wt % per total weight of copolymer (for example, Eudragit® RL, Evonik) or 2.0 to 7.99 wt % (for example, Eudragit® RS, Evonik), or a polymer mixture thereof.

As the content of unit of trimethylammonium chloride methacrylate increases, the rates of water penetration and the drug release increase. As the content decreases, the rates of water penetration and the drug release decrease. For example, when the content of unit of trimethylammonium chloride methacrylate is 8.0 to 15.0 wt % (for example, Eudragit® RL, Evonik), the water penetration and the drug release become faster relatively. When the content of unit of trimethylammonium chloride methacrylate is 2.0 to 7.99 wt % (for example, Eudragit® RS, Evonik), the water penetration and the drug release become slower relatively. All polymers included in the water insoluble ammonium methacrylate copolymer do not dissolve in water or a solvent used in the dissolution test due to the water insoluble property, and are hardly affected by pH condition.

The polyvinyl acetate can be used alone or together with polypyrrolidone in a physical mixture. The polyvinyl acetate can have a weight-average molecular weight of 50,000 to 1,000,000 Da, for example, 100,000 to 800,000 Da or 300,000 to 600,000 Da. For example, polypyrrolidone has a molecular weight of 10,000 to 500,000 Da, such as 10,000 to 200,000 Da. When polyvinyl acetate is mixed with polypyrrolidone, the mixing weight ratio (polyvinyl acetate weight:polypyrrolidone weight) is 9.9:0.1 to 5:5, specifically 9.5:0.5 to 6:4, or 9:1 to 7:3, or more specifically 9:1 to 8:2. By including polyvinyl acetate in the pellet, the release of drug contained in the pellet can be controlled easily and efficiently.

Polyvinyl acetate can include Kollicoat® SR30D and Kollidon® SR. Kollicoat® SR30D is a solution including 30 wt % of dispersed polyvinyl acetate and polypyrrolidone at a weight ratio (polyvinyl acetate weight:polypyrrolidone weight) of 9:1 in order to obtain the dispersion stability. Kollidon® SR includes a physical mixture of polyvinyl acetate and polypyrrolidone at a weight ratio of 8:2. The polyvinyl acetate has a weight-average molecular weight of 50,000 to 1,000,000 Da, for example, 100,000 to 800,000 Da or 300,000 to 600,000 Da. The polypyrrolidone has a weight-average molecular weight of 10,000 to 500,000 Da, for example 10,000 to 200,000 Da. In an example of the present invention, the polyvinyl acetate can be Kollidon® SR.

The mixing ratio of water insoluble ammonium methacrylate copolymer and polyvinyl acetate (water insoluble ammonium methacrylate copolymer weight:polyvinyl acetate weight) in the pellet can be 1:0.05 to 20 by weight, or specifically 1:0.1 to 10 by weight. If the mixing ratio of water insoluble ammonium methacrylate copolymer and polyvinyl acetate is outside of the ranges, the arrangement of polymer chain can be different, thereby causing the excessive late phase delayed-release effect.

The weight ratio of active ingredient and a polymer mixture of water insoluble ammonium methacrylate copolymer and polyvinyl acetate (weight of active ingredient: weight of mixture of water insoluble ammonium methacrylate copolymer and polyvinyl acetate) in the pellet can be 1:1 to 100, specifically 1:5 to 80, or 1:10 to 60. The weight ratio of active ingredient and a polymer mixture is less than the ranges (that is, the amount of active ingredient is excessively large), the pellet can be broken and crumbed largely due to the poor pellet formation. When the weight ratio of active ingredient and a polymer mixture is larger than the ranges (that is, the amount of active ingredient is excessively small), the formulation size becomes excessively large.

The active ingredient can be at least one selected from the group consisting of drug itself, pharmaceutically acceptable salts, isomers and a mixture thereof.

The active ingredients applicable to the present invention can be any one requiring controlled release without limitation, and for example, includes the following active ingredients:

Antipsychotics such as chlorpromazine, thioridazine, loxapine, molindone, clozapine, olanzapine, quetiapine, risperidone, ziprasidone, fluphenazine, haloperidol, perphenazine, trifluoperazine, pimozide, aripiprazole, prochlorperazine, thiothixine, paliperidone;

Antidepressants such as mirtazapine, bupropion, amoxapine, phenelzine, tranylcypromine, citalopram, fluoxetine, fluvoxamine, paroxetine, sertraline, venlafaxine, maprotiline, trazodone, nefazodone, amitriptyline, clomipramine, desipramine, dexepin, imipramine, nortriptyline, protriptyline, and trimipramine, drugs for degenerative nerve disease such as amantadine, benztropine mesylate, carbidopa 및 levodopa, donepezil, bromocriptine, pergolide, pramipexole, ropinirole ADHD drugs such as methylpenidate, and atomoxetine, Anticonvulsants such as pregabalin, lacosamide, carbamazepine, clonaepam, ethosuximide, felbamate, gabapentin, lamotrigine, levetiracetam, oxcarbazepine, phenobarbital, phenytoin, primidone, tiagabine, topamax, valproic acid, divalproex sodium, and zonisamide;

Anti-anxiety drugs, sedatives or hypnotics such as alprazolam, lorazepam, oxazepam, chlordiazepoxide, clorazepate, diazepam, halazepam, midazolam, triazolam, zaleplon, zolpidem, estazolam, temazepam, flurazepam, quazepam, meprobamate, phenobarbita, chloral hydrate, ethchlorvinol, glutethimide, pentobarbital, and secobarbital;

Erectile dysfunction (impotence) drugs such as sildenafil, vardenafil, alprostadil, tadalafil, mirodenafil and udenafil;

Immuno-suppressants such as azathioprine, cyclosporine, mycophenolate mofetil, sirolimus, and tacrolimus;

antihypertensive drugs such as doxazosin mesylate, prazosin hydrochloride, terazosin hydrochloride, benazepril, captopril, clonidine hydrochloride, enarapril, hydralzine hydrochloride, labetalol hydrochloride, losartan potassium, methyldopate hydrochloride, minoxidil, moexipril, trandolapril, candesartan, irbesartan, losartan, telmisartan, valsartan, guanabenz acetate, guanadrel sulfate, guanfacine hydrochloride and reserpine;

Beta-adrenergic blocking drugs such as acebutolo, atenolol betaxolol, bisoprolol, carteolol, carvedilol, labetalol, metoprolol, nadolol, penbutolol, pindolol, propranolol, sotalol, and timolol;

Calcium channel blockers such as amlodipine, bepridil, diltiazem, felodipine, Isradipine nicardipine, nifedipine, nimodipine, nisoldipine, and verapamil;

Lipid-lowering drugs such as fenofibrate, gemfibrozil, niacin, atrovastatin, fluvastatin, lovastatin, pravastatin, and simvastatin;

mosapride, itopride, domperidone, trunebutine, metoclopramide, bisacodyl, Diphenoxylate hydrochloride 및 atropine sulphate, docusate, Loperamide, Magnesium salt, Metoclopramide, and Ursodiol;

Coagulants and anticoagulants such as Clopidogrel bisulfate, phytonadione, ticlopidine and warfarin sodium;

Vasodilators such as limaprost, beraprost, and sarpogrelate;

Anti-migraine drugs such as almotriptan, ergotamine tartrate, Frovatriptan Methysergide Maleate, Methysergide Maleate, and zolmitriptan;

Anti-rheumatic drugs such as auranofin, azathioprine, cyclosporin, Hydroxychloroquine sulphate, leflunomide, methotrexate, penicillamine, and sulfasalazine; Non-steroidalAnti-inflammatory drugs such as acetaminophen, aspirin, diclofenac, etodolac, fenoprofen, ibuprofen, ketoprofen, naproxen, indomethacin, ketololac, sulindac, tolmetin, meclofenamate, mefenamic acid nabumetone meloxicam, piroxicam, elecoxib and rofecoxib;

Opioids such as buprenorpine, codein, fentanyl, hydrocodone, hydromorphone, levorphanol, meperidine, morphine, oxycodone, pentazocine, and propoxyphene;

Non-opioid pain killing drugs such as tramadol and tapentadol;

anti-cancer drugs such as imatinib, erlotinib, sunitinib orafenib, lapatinib, gefitinib, dasatinib and lenalidomide;

anti-*mycobacterium* drugs such as aminosalicylate, clofazimine, cycloserin, ethionamide, and rifabutin;

Antiparasitic drugs such as albendazole, ivermectin, mebendazole, and praziquantel;

anti-viral drugs such as valacyclovir, didanosine, famciclovir valganciclovir, indinavir lamivudine, nelfinavir mesylate, nevirapine, ritonavir, stavudine, and oseltamivir phosphate;

Beta-lactam antibiotics such as amoxicillin and potassium clavulanate, ampicillin, cefroxime sodium, cefuroxime acetyl, penicillin G and Y salt, cefditoren, cefixime, and cloxacillin sodium;

Macrolide antibiotics such as erythromycin estolate, erythromycin ethylsuccinate, and drythromycin stearate;

Fluoro-quinolones drugs such as ciprofloxacin and enoxacin;

Tetracyclines such as demeclocycline hydrochloride, doxycycline calcium, tetracycline and tetracycline hydrochloride;

Alkylating agents such as Altretamine, busulfan chlorambucil, melphalan, cyclophosphamide, procarbazine hydrochloride and temozolomide;

Antimetabolite such as methotrexate, mercaptopurine and thioguanine;

hormonal Drug and antagonist such as bicalutamide, flutamide, nilutamide, aminoglutethimide, anastrozole, exemestan, letrozole, tamoxifen citrate and toremifene citrate;

Mitotic inhibitors such as etoposide phosphate;

Arrhythmia drugs such as amiodarone hydrochloride, digoxin, disopyramide phosphate, dofetillide flecainide acetate, mexiletine hydrochloride, moricizine hydrochloride, procainamide hydrochloride, propafenone hydrochloride, quinidine sulfate, quinidine gluconate, sotalol hydrochloride, and tocainide;

nitrates drugs such as isosorbide dinitrate, nitroglycerin and sodium nitroprusside;

Ophthalmic glaucoma drugs such as acetazolamide, Dichlorphenamide and methazolamide;

drug for Acid—pepsin treatment such as aluminum carbonate, aluminum hydroxide, magnesium hydroxide, sodium bicarbonate, calcium carbonate and magaldrate;

Bismuth salt, Cimetidine, Famotidine, Nizatidine, Ranitidine, misoprostol, Lansoprazole, Omeprazole, Pantoprazole, Rabeprazole, and sulcrafate;

Antiemetics such as buclizine, cyclizine, dimenhydrinat, diphenhydramine, eclizine, dronabinol, chlorpromazine, perphenazine, prochlorperazine, promazine, thiethylperazine, triflupromazine, dolasetron, granisetron, ondansetron, dexamethasone, lorazepam, granisetron, ramosetron, and aprepitant;

Hematopoietic drugs such as ferric salts;

Adrenal hormones such as cortisone, hydrocortisone, methylprednisolone, prednisolone, triamcinolone, betamethasone, dexamethasone, and fludrocortisone;

Antidiabetic drugs such as acarbose, metformin, nateglinide, repaglinide, acetohexamide, Chlorpropamide, tolazamide, tolbutamide. glimepiride, glipizide, glyburide, Pioglitazone and osiglitazone;

Contraceptives such as norethindrone, norgestrel, and levonorgestrel;

Female sex hormones such as estradiol and its esters, estrogen, estropipate medroxyprogesterone mifepristone, norethindrone acetate, progesterone raloxifene;

Thyroid and anti-thyroid drugs such as iodide, levothyroxine sodium,

Diuretic drugs such as Liotrix, methimazole, Amiloride hydrochloride, bumetanide, ethacrynic acid, furosemide, torsemide, hydrochlorothiazide, chlorthalidone, indapamide, metolazone, Polythiazide, quinethazone, trichlormethiazide, spironolactone, triamterene;

Electrolytic substances such as Chelated magnesium, magnesium chloride, magnesium hydroxide, magnesium oxide, potassium salts;

Gout-treating agents such as allopurinol, colchicine, probenecid, sulfinpyrazone;

Asthma treatment drugs such as albuterol sulfate, montelukast sodium, theophylline, zileuton;

Antihistamines such as acrivastine, azatadine, brompheniramine maleate, carbinoxamine maleate, cetirizine hydrochloride, chlorpheniramine maleate, diphenhydramine hydrochloride, mastine fumarate, cyproheptadine hydrochloride, fexofenadine, hydroxyzine, loratadine, desloratadine;

cough-suppressive drugs or cold-treating drugs such as dextromethorphan hydrobromide, guaifenesin, pseudoephedrine hydrochloride; and Health Functional Food.

In an embodiment, an average diameter of pellet can be 5 to 4500 μm, specifically 10 to 4500 μm or 20 to 2000 μm, or more specifically 50 to 1500 μm or 100 to 1200 μm. When the size of pellet is smaller than the ranges, the pellet loss due to the electrostatic force, the inconvenience in the preparation process, and the needs of excessive production time and coating solution can be caused. When the size of pellet is larger than the ranges, it can cause the administration inconvenience of patient, and non-uniform formulation.

The shape of pellet cannot be defined specifically, and for example, includes Cylindrical, spherical, rugby ball shaped, oval, disc, cubic, rectangular, and other polyhedral shapes.

In order to form the uniform polymer coating layer on the pellet, the pellet can have certain shape and size.

The pellet can be prepared by various methods, but not limited. For example, the pellet can be prepared by hot melt extrusion method in order to increase bioavailability and/or slow-release property of active ingredient. The hot melt extrusion method has been used in the plastics industry and then introduced to the pharmaceutical industry. Thus, the hot melt extrusion method can be used for the pharmaceuticals, as long as the stability of drug is guaranteed.

The method of preparing the pellet includes the steps of mixing active ingredient, water insoluble ammonium methacrylate copolymer, and polyvinyl acetate; performing hot-melt extrusion of the mixture, and optionally, drawing and/or cutting the extruded product.

The hot-melt extruding step can be performed with a general extruder such as hot-melt extruder. The extruder includes single screw or double screws. The mixture for preparing the pellet can be put to pass through a container which includes a screw with different controlled temperature at each region. For example, the extruder can be equipped with double screws, which is advantageous for providing mechanical energy and for conveying, mixing and compressing the mixture. The extruder can be provided with a heating device and a cooling device, as required. The container which includes a screw with different controlled temperature at each region can be divided to two or three regions. For example, the hot-melt extrusion can be performed at 50 to 250° C., specifically 60 to 200° C., or more specifically 70 to 180° C. The temperature of each region can be controlled different, so long as the temperature is within the ranges. For example, the temperature can be adjusted to relatively low temperature, for example, 50 to 130° C. at a mixture inlet region; to the highest temperature at a middle region where polymer melting and the effective mixing of active ingredient can occur, for example 120 to 250° C.; and to lower temperature than the middle region at outlet region, for example, 100 to 180° C., but not limited thereto.

The mixing and kneading step, hot-melt extruding step performed in an extruder, can be varied depending on the number, shape, length, and arrangement of screw. By considering the easy melt-extrusion, the extruding step can be performed by using the extruder with the short retention time of mixture and low shearing force. Such condition is more important to use thermo-sensitive active ingredient.

The rotation speed of screw can affect the quality of pellet. For example, if the rotation speed of screw is too low, retention time of mixture unnecessarily lengthens, which is not preferable. If the rotation speed of screw is too fast to the input rate of mixture, the porous pellet can be produced, and excessive force applies to the extruder. Accordingly, the rotation speed of screw is preferably 30 to 300 rpm.

The air is introduced together with the mixture to the extruder cylinder. In order to remove the air, remaining moisture in components and solvent and to easily prepare the nonporous pellet with high density, the extruder cylinder can be connected to the vacuum device.

The content in the extruder can be extruded through the head of extruder which can be formed at various shapes. Typically, the shape of head can be circular shape with a fixed diameter, for example, 0.1 to 10 mm, triangular, rectangular, or polygonal shape. For example, the extruder includes the circular-shaped head.

In an embodiment, the strand extruded from the head can wind up by winder, with drawing, and the width of strand can be adjusted by winding speed. The width of strand can be measured continuously by using laser detector.

In another embodiment, the strand extruded from the head can be cut by using the cutting device. The extruded strand can be cut shortly after the melt extruding by using the cutting device located in front of the head, or cut after the extruded strand is cooled by passing through the tube filled with air or medium (air, solvent or solution), by using the cutting device located after the cooling tube. Alternatively, after the melt extrusion, the extruded strand can be cut by using a separate cutting device. For example, a cutting device equipped with a rotating cutting knife can be used for the cutting step. The shape and size of pellet can be prepared differently, depending on the shape, the rotating direction and the rotating speed of knife, the feeding rate, and the like.

Generally, the arrangement and the interaction of feeding device of mixture, a melt extruder, a conveyer, a winder and a cutting device is an important factors affecting the shape, amount, quality and reproducibility of pellet, they can be suitably controlled considering the desired shape, amount, quality, etc. of pellet, which is known to the ordinarily skilled person in the art.

The hot melt extrusion method can remove the need of solvent, make the manufacturing process be simple, maintain the crystallinity of drug or changes the crystalline structure into amorphous structure, and shorten the production time. In addition, the shape and size of pellet can be easily changed by selecting the extrusion die, the drawing method, and cutting method.

If the drug has a low stability at a high temperature, the addition of plasticizer can lower the operation temperature.

In the preparation process of pellet according to the hot melt extrusion method, various biologically inert additives can used by considering the additional objects such as the efficiency of hot melt extrusion, the stability of active ingredient, appearance, color, protection, maintenance, binding property, improvement in the formulation property and the preparation process.

The kinds, using method, and adding method to the pellet of the biologically-inert additives can be known to an ordinarily skilled person in the art and can be changed variously.

The biologically-inert additives added to the pellet can include at least one selected from the group consisting of plasticizer, lubricant, coloring agent, flavoring agents, sweetening agents, surfactant, stabilizers, antioxidants, foaming agents, anti-foaming agents, paraffins, waxes, and a mixture thereof. The kind and amount of exemplified additives can be selected suitably by an ordinarily skilled person in the art and can be changed variously.

For example, the plasticizer can be used at an amount of 30 wt % or less (for example, 0 to 30 wt % or 0.1 to 30 wt %), specifically 20 wt % or less (for example, 0 to 20 wt % or 0.1 to 20 wt %), or more specifically 10 wt % or less (for example, 0 to 10 wt % or 0.1 to 10 wt %) with respect to total dry weight of polymer used in the pellet.

The examples of plasticizer includes at least one selected from the group consisting of triethyl citrate, dibutyl phthalate, diethyl phthalate, dibutyl sebacate, diethyl sebacate, tributyl citrate, acetyl triethyl citrate, acetyl triethyl citrate, propylene glycol, triacetin, polyethylene glycols, cetyl alcohol, stearyl alcohol, and cetostearyl alcohol, but not limited thereto. Specifically, the plasticizer can be at least one selected from the group consisting of triethyl citrate, dibutyl phthalate, diethyl phthalate dibutyl sebacate and diethyl sebacate.

The lubricant can be used at an amount of 0.01 to 30 wt % with respect to total dry weight of polymer used in the pellet. The lubricant improves the flowability of mixture fed to the hot-melt extruder and reduces the friction inside screw, thereby extruding the mixture efficiently. The amount of lubricant can be 0.01 wt % or more by considering the functions of lubricant in the present invention, and 30 wt % or less by considering the addition efficiency of lubricant.

The examples of plasticizer includes at least one selected from the group consisting of stearic acid, glyceryl behenate, glyceryl monostearate, magnesium stearate, calcium stearate, silica, talc, and magnesium silicate Polymer Coating Layer In the controlled release pharmaceutical composition, the polymer coating layer formed on the pellet surrounds the surface of pellet and thus, effectively control the release of active ingredient contained in the pellet.

Particularly, the polymer coating layer can function as a slow-release matrix, and effectively control the release pattern of active ingredient by forming the coating layer on the surface of pellet. By adjusting the weight ratio of coating layer, the pharmaceutical composition with ideal release pattern can be easily prepared.

The coating layer can include a water insoluble ammonium methacrylate copolymer. The water insoluble ammonium methacrylate copolymer can be poly(ethylacrylate/methylmethacrylate/trimethyl ammonium chloride methacrylate). The water insoluble ammonium methacrylate copolymer can have a molecular weight of 20,000 to 500,000 Da, for example, 50,000 to 300,000 Da, or 100,000 to 200,000 Da.

In an embodiment, the water insoluble ammonium methacrylate copolymer can be poly(ethylacrylate/methylmethacrylate/trimethyl ammonium chloride methacrylate) where the moisture-penetrating property can be various, as it depends on the unit of trimethyl ammonium chloride methacrylate. For example, the water insoluble ammonium methacrylate copolymer can be the polymer including the unit of trimethyl ammonium chloride methacrylate at an amount of 8.85 to 11.96 wt % per total weight of copolymer (for example, Eudragit® RL, Evonik) or 2.0 to 7.99 wt %((for example, Eudragit® RS, Evonik), or a polymer mixture thereof.

As the content of unit of trimethyl ammonium chloride methacrylate increases, the rates of water penetration and the drug release increase. As the content decreases, the rates of water penetration and the drug release decrease. For example, when the content of unit of trimethyl ammonium chloride methacrylate is 8.0 to 15.0 wt % (for example, Eudragit® RL, Evonik), the water penetration and the drug release become faster relatively. When the content of unit of trimethyl ammonium chloride methacrylate is 2.0 to 7.99 wt % (for example, Eudragit® RS, Evonik), the water penetration and the drug release become slower relatively. All polymers included in the water insoluble ammonium methacrylate copolymer do not dissolve in water or a solvent used in the dissolution test due to the water insoluble property, and are hardly affected by pH condition.

The water insoluble ammonium methacrylate copolymer in the pellet and the water insoluble ammonium methacrylate copolymer in the polymer coating layer can be the same or different each other, in aspect of the content ratio and the molecular weight of unit, and total molecular weight of polymer, and can be selected suitably by considering the kind of active ingredient.

The weight of polymer coating layer formed on the pellet can be 1 to 500% (0.01 to 5 times), for examples, 2 to 300%(0.02 to 3 times), 3 to 100% (0.03 to 1 time), or 4 to 50% (0.04 to 0.5 time), with respect of the total weight of pellet.

The average thickness of polymer coating layer can be 2 to 500 μm, specifically 3 to 400 μm, or more specifically 4 to 250 μm. The average thickness is preferably 2 μm or higher by considering the controlled release of active ingredient, and 500 μm or less by considering the effective release of active ingredient in the intestine.

The polymer coating layer can be formed by a coating solution including the water insoluble ammonium methacrylate copolymer and a suitable solvent. The solvent can be at least one selected from the group consisting of water and $C_{1-4}$ linear or branched alcohol (for example, methanol, ethanol, or isopropyl alcohol). The concentration of water insoluble ammonium methacrylate copolymer in the coating solution can be 1 to 40 wt %.

According to an embodiment, the polymer coating layer can be prepared by using any coating apparatus such as general coater, fluid bed coater, fluid bed processor or fluid bed granulator. Specifically, fluidized bed system with bottom spray and centrifugal granulator, for example, Granurex® (Freund), and the like can be used in the coating process.

In the coating process of pellet, various biologically-inactive additives can used for the polymer coating layer or the coating solution, by considering the additional objects such as the efficiency of hot melt extrusion, the stability of active ingredient, appearance, color, binding property, improvement in the formulation property and the preparation process.

The biologically-inactive additives added to the pellet can includes at least one selected from the group consisting of plasticizer, lubricant, coloring agent, flavoring agents, sweetening agents, surfactant, stabilizers, antioxidants, foaming agents, paraffins, waxes, and anti-foaming agents. The biologically-inactive additives can be the same as described above.

The controlled release pharmaceutical composition of present invention has a dissolution pattern where 80 wt % of active ingredient releases for 8 to 24 hours, when the dissolution test is performed according to the paddle method of dissolution test described in the Korean Pharmacopoeia Eighth edition (KP VIII) which is specifically performed at 100 rpm by using 500~1000 ml of one or more dissolution solution selected from a buffer solution with pH 1.2, a buffer solution with pH 4.0, a buffer solution with pH 6.8, water, and 0.1N HCl solution.

Oral Formulation

In another embodiment, the oral formulation including the controlled release pharmaceutical composition can be provided. The oral formulation has a dissolution pattern where 80 wt % of active ingredient releases for 8 to 24 hours. Accordingly, the oral formulation can release the active ingredient slowly, thereby lasting the efficacy for a relatively long time.

The unit dosage of oral formulation can include 0.005 to 2000 mg of active ingredient, and can show the desired efficacy even by administrating once or twice daily, because it achieves the optimum dissolution pattern of active ingredient.

The oral formulation can be prepared to general type which has been known in the art, without the limitation.

According to an embodiment, the oral formulation can be capsules, tablets (plain tablets, double tablets, chewing tablets, rapid-disintegrable tablets), dry syrup formulation, syrup, jelly-type formulation or a granule, preferably capsule or tablet, or more preferably rapid-disintegrable tablets.

The oral formulation can include further at least one selected from the group consisting of excipient, disintegrator, binder, lubricant, colorant, flavor, sweetener, surfactant, stabilizers, foaming agents and antioxidants, as well as the controlled release pharmaceutical composition.

For example, the capsule can be prepared by mixing the controlled release pharmaceutical composition with at least one additive selected from the group consisting of lubricant, excipient and the like, and filling the mixture to soft capsule. The plain tablet and chewing tablet can be can be prepared by mixing the controlled release pharmaceutical composition with at least one additive selected from the group consisting of excipient, disintegrator, binder, lubricant, colorant, flavor, sweetener, and the like, and tableting the mixture. The syrup can be prepared by homogeneously dispersing the controlled release pharmaceutical composition in syrup, and preventing the active ingredient from releasing into the syrup during the storage.

In case that the oral formulation is in the form of rapid-disintegrable tablet to improve the administration convenience of patient, rapid-disintegrable tablet can be administered without water due to the disintegration in mouth, resulting in easy administration for old people, patient with dysphagia or reluctance to swallowing the tablet and etc. In addition, the dissolution pattern of active ingredient in the rapid-disintegrable tablet can be controlled by the pellets in the pharmaceutical composition of an embodiment of the present invention, so as to achieve the best efficacy.

Particularly, because the rapid-disintegrable tablet stays in a mouth quite a while, the bitter taste of drug needs be shielded but is not sufficient by adding the sweetening agent and flavor. The controlled release pharmaceutical composition of present invention can prevent the drug from releasing in a mouth for 1 minutes or longer (for example, 3 minutes or longer), and thus remove the resistance to the drug administration. The rapid-disintegrable tablet can be prepared by mixing the controlled release pharmaceutical composition with rapid-disintegrable agent such as WOWTAB®, Zydis®, OraSolv®, DuraSolv®, QuickSolv®, FlashTab®, AdvaTab®, Lyoc®, FlashDose®, Frosta® and the like. The mixing ratio and method of rapid-disintegrable agent can be selected suitably by an ordinarily skilled person in the art.

In the formulation process as described above, the damage of polymer coating layer can be prevented preferably by applying the tablet pressure within the suitable range or adding a buffering agent. In the formulation process, the tableting method includes the tableting by direct compression where the controlled release pharmaceutical composition is mixed with excipients and tableted without granulating process; the tableting after granulation where the controlled release pharmaceutical composition is firstly granulated and then tableted with the addition of excipients; and the tableting after granulation with excipients where the controlled release pharmaceutical composition is firstly with excipients and then tableted with the mixture or with the addition of other excipients.

The controlled release pharmaceutical composition of present invention can easily control the dissolution patter of active ingredient as desired, minimize the side-effect by preventing the rapid release of active ingredient into blood, maintain the effective blood level of active ingredient for a certain time, and shield bitter taste in a mouth for a certain time, resulting in maximization of the drug efficacy at oral administration.

DETAILED DESCRIPTION OF THE EMBODIMENTS

Hereinafter, the examples can be provided in order to give an understanding of the present invention. However, the following examples are only intended to illustrate the invention, but are not intended to limit the invention to these.

The analyzing methods used in the examples are referred to Reference Examples 1 and 2.

Reference Example 1. Drug Dissolution Test

The dissolution test of a plain pellet, a pellet with controlled release coating, plain tablet, capsule, chewing tablet and rapid-disintegrable tablet was performed according to the paddle method of dissolution test described in "36. Dissolution test" of the Korean Pharmacopoeia Eighth edition (KP VIII). The dissolution solution was 500~1000 ml of one selected from a buffer solution with pH 1.2, a buffer solution with pH 4.0, a buffer solution with pH 6.8, water, and 0.1N HCl and the rotation speed was 50~100 rpm.

The dissolute was analyzed with High performance liquid chromatography (HPLC) under the following condition:

Mobile phase: mixed solution including 1 L of acetonitrile and a solution where 21.76 g of monopotassium phosphate was dissolved in 4 L of water, and adjusted by phosphoric acid to pH2.0, Column: XBridge phenyl. 150×4.6 mm, 3.5 μm, Flow rate: 1.0 Ml/min, Column Temperature: 27° C., Wavelength: 238 nm, Injection volume: 10 μl, Standard solution: 180.0 mg of paliperidone was dissolved with the dissolution solution in 100 Ml flask to be adjusted to standard line and then 1.0 Ml of solution was added to 100 Ml flask and added with the same dissolution solution to be adjusted to standard line, to obtain the standard solution.

Reference Example 2. Drug Amount Analysis

The active ingredient contained in a plain pellet, a pellet with controlled release coating, plain tablet, capsule, chewing tablet and rapid-disintegrable tablet was analyzed by mixing with solution, centrifuging to obtain the supernatant, filtering and diluting the supernatant. Thus, the analyzing solution was produced and then performed with HPLC under the following condition:

Mobile phase: mixed solution including 1 L of acetonitrile and a solution where 21.76 g of monopotassium phosphate was dissolved in 4 L of water, and adjusted by phosphoric acid to pH2.0,
Column: XBridge phenyl. 150×4.6 mm, 3.5 μm
Flow rate: 1.0 Ml/min
Column Temperature: 27° C.
Wavelength: 238 nm
Injection volume: 5 μl
Standard solution: 180.0 mg of paliperidone was dissolved with the dissolution solution in 100 Ml flask to be adjusted to standard line and then 10.0 Ml of solution was added to 100 Ml flask and added with the same dissolution solution to be adjusted to standard line, to obtain the standard solution.

Example 1. Preparation of Pellet 15.8 g of paliperidone, 47.4 g of Eudragit® RL PO (Evonik; 10 wt % of the unit of trimethyl ammonium chloride methacrylate) and 236.8 g of Kollidon® SR were mixed and fed to PET-015 (Vanho, Korea) double screw extruder which was divided to three regions for different temperature control by setting the temperature suitably within the range of 70 to 140° C. (inlet region: 70° C., mixing region: 140° C., extruding region: 125° C., rotation speed: 100 rpm). The strand extruded from die-head of extruder had a constant width of about 800 um (micrometer) with winder, and was cut using a separating cutting device after termination of extruding process, to produce a cylinder-shaped strand having a height of about 800 um.

Example 2

2A: Formation of Polymer Coating Layer on the Pellet 3.08 g of Eudragit® RS 100 (Evonik; 5 wt % of the unit of trimethyl ammonium chloride methacrylate) was dissolved in a mixed solution of 44 g of ethanol and 2.35 g of water, and added with 0.308 g of dibutyl sebacate and 1.5 g of talc to produce the polymer coating solution.

20 g of the pellet obtained in Example 1 was mixed with 0.05 g of Aerosil, fed to mini-glatt equipped with microkit (Glatt, Germany) as a seed, and was coated by spraying the coating solution according to bottom spray manner. After spraying the coating solution, the coated pellet was dried, to obtain 22 g of controlled release pharmaceutical composition including the drug.

As a test result of the produced core (pellet) according to the drug amount analysis (HPLC; Reference Example 2), the amount of drug (paliperidone) was about 5.3 wt %. As a test result of the dissolution test (Reference Example 1), controlled release pharmaceutical composition released the drug slowly for 2 to 24 hours and the dissolution pattern was close to zero order kinetics. The test results are summarized in Table 1.

TABLE 1

| Time (hour) | Dissolution rate (%) |
| --- | --- |
| 1 | 0 |
| 2 | 0 |
| 4 | 10.0 |
| 6 | 22.9 |
| 8 | 33.9 |
| 12 | 58.4 |
| 15 | 71.7 |
| 18 | 85.0 |
| 21 | 96.1 |
| 24 | 98.0 |

2B: Formation of Polymer Coating Layer on the Core 2.77 g of Eudragit® RS 100 (Evonik; 5 wt % of the unit of trimethyl ammonium chloride methacrylate) and 0.308 g of Eudragit® RL 100 (Evonik; 10 wt % of the unit of trimethyl ammonium chloride methacrylate) was dissolved in a mixed solution of 44 g of ethanol and 2.35 g of water, and added with 0.308 g of dibutyl sebacate and 1.5 g of talc to produce the polymer coating solution.

20 g of the pellet obtained in Example 1 was mixed with 0.05 g of Aerosil, fed to mini-glatt equipped with microkit (Glatt, Germany) as a seed, and was coated by spraying the coating solution according to bottom spray manner. After spraying the coating solution, the coated pellet was dried, to obtain 21.8 g of controlled release pharmaceutical composition including the drug.

As a test result of the produced core (pellet) according to the drug amount analysis (HPLC; Reference Example 2), the amount of drug (paliperidone) was about 5.3 wt %. As a test result of the dissolution test (Reference Example 1), controlled release pharmaceutical composition released the drug slowly for 1 to 20 hours and the dissolution pattern was close to zero order kinetics. The test results are summarized in Table 2.

TABLE 2

| Time (hour) | Dissolution rate (%) |
| --- | --- |
| 1 | 0 |
| 2 | 3.6 |
| 4 | 12.1 |
| 6 | 32.1 |
| 8 | 55.2 |
| 12 | 81.4 |
| 15 | 87.9 |
| 18 | 96 |
| 21 | 98 |
| 24 | 100.4 |

Comparative Example 1

15.8 g of paliperidone and 284.2 g of Eudragit® RS PO (Evonik) were mixed and fed to PET-015 (Vanho, Korea) double screw extruder which was divided to three regions for different temperature control by setting the temperature suitably within the range of 70 to 140° C. (inlet region: 70° C., mixing region: 140° C., extruding region: 125° C.; rotation speed: 100 rpm). The strand extruded from die-head of extruder had a constant width of about 800 um (micrometer) with winder, and was cut using a separating cutting device after termination of extruding process, to produce a cylinder-shaped strand having a height of about 800 um.

3.08 g of Eudragit® RS 100 (Evonik) was dissolved in a mixed solution of 44 g of ethanol and 2.35 g of water, and added with 0.308 g of dibutyl sebacate and 1.5 g of talc to produce the polymer coating solution.

20 g of the pellet obtained in Example 1 was mixed with 0.05 g of Aerosil, fed to mini-glatt equipped with microkit (Glatt, Germany) as a seed, and was coated by spraying the coating solution according to bottom spray manner. After spraying the coating solution, the coated pellet was dried, to obtain 22 g of controlled release pharmaceutical composition including the drug.

As a test result of the produced core (pellet) according to the drug amount analysis (HPLC; Reference Example 2), the amount of drug (paliperidone) was about 5.3 wt %. As a test result of the dissolution test (Reference Example 1), controlled release pharmaceutical composition released 60% of drug within 24 hours. The test results are summarized in Table 3.

TABLE 3

| Time (hour) | Dissolution rate (%) |
|---|---|
| 1 | 0 |
| 2 | 0 |
| 4 | 4.3 |
| 6 | 9.5 |
| 8 | 16.9 |
| 12 | 27.3 |
| 15 | 34.4 |
| 18 | 40.0 |
| 21 | 44.9 |
| 24 | 49.8 |

Example 4

15.8 g of paliperidone, 47.4 g of Kollidone® SR, and 236.8 g of Eudragit® RL PO (Evonik) were mixed and fed to PET-015 (Vanho, Korea) double screw extruder which was divided to three regions for different temperature control by setting the temperature suitably within the range of 70 to 140° C. (inlet region: 70° C., mixing region: 140° C., extruding region: 125° C.; rotation speed: 100 rpm). The strand extruded from die-head of extruder had a constant width of about 800 um (micrometer) with winder, and was cut using a separating cutting device after termination or extruding process, to produce a cylinder-shaped strand having a height of about 800 um.

3.08 g of Eudragit® RS 100 (Evonik) was dissolved in a mixed solution of 44 g of ethanol and 2.35 g of water, and added with 0.308 g of dibutyl sebacate and 1.5 g of talc to produce the polymer coating solution.

20 g of the pellet obtained in Example 1 was mixed with 0.05 g of Aerosil, fed to mini-glatt equipped with microkit (Glatt, Germany) as a seed, and was coated by spraying the coating solution according to bottom spray manner. After spraying the coating solution, the coated pellet was dried, to obtain 12 g of controlled release pharmaceutical composition including the drug.

As a test result of the produced core (pellet) according to the drug amount analysis (HPLC; Reference Example 2), the amount of drug (paliperidone) was about 5.3 wt %. As a test result of the dissolution test (Reference Example 1), controlled release pharmaceutical composition released the drug slowly for 24 hours. The test results are summarized in Table 4.

TABLE 4

| Time (hour) | Dissolution rate (%) |
|---|---|
| 1 | 0 |
| 2 | 0.8 |
| 4 | 7.1 |
| 6 | 13.4 |
| 8 | 37.7 |
| 12 | 71.7 |
| 15 | 86.6 |
| 18 | 95.0 |
| 21 | 98.1 |
| 24 | 101.2 |

Example 4. Encapsulation 10 g of the controlled release pharmaceutical composition obtained in Example 2A was added with 0.5 g of Aerosil, and filled to size-3 capsule (gelatin capsule, Suheung capsule), to 170 mg per each capsule.

The filled capsule was tested according to the dissolution test of Reference Test 1 to show the test result in Table 5. The capsule released the drug (paliperidone) slowly for 2 to 24 hours and the dissolution pattern was close to zero order kinetics, which was the same result as the dissolution pattern of the controlled release pharmaceutical composition without encapsulation in Example 2-A.

TABLE 5

| Time (hour) | Dissolution rate (%) |
|---|---|
| 1 | 0 |
| 2 | 0 |
| 4 | 11.0 |
| 6 | 22.0 |
| 8 | 33.6 |
| 12 | 57.1 |
| 15 | 72.3 |
| 18 | 84.0 |
| 21 | 94.6 |
| 24 | 97.0 |

What is claimed is:

1. A controlled release pharmaceutical composition comprising:
    a melt-extruded pellet consisting of a water-insoluble ammonium methacrylate copolymer, a polyvinyl acetate, optionally polypyrrolidone in a physical mixture with said polyvinyl acetate, and an antipsychotic drug as an active ingredient; and
    a polymer coating layer formed on the pellet comprising a water-insoluble ammonium methacrylate copolymer, wherein:
    the water-insoluble ammonium methacrylate copolymer of the pellet and the water-insoluble ammonium methacrylate copolymer of the polymer coating layer are a same or different poly(ethylacrylate/methylmethacrylate/trimethyl ammonium chloride methacrylate) copolymer, and
    the poly(ethylacrylate/methylmethacrylate/trimethyl ammonium chloride methacrylate) copolymer is a polymer having a content of trimethyl ammonium chloride methacrylate unit of 8.0 wt % to 15.0 wt % per weight of copolymer, a polymer having a content of trimethyl ammonium chloride methacrylate unit of 2.0 wt % to 7.99 wt % per weight of copolymer, or a mixture thereof, wherein a mixing ratio of the water insoluble ammonium methacrylate copolymer and polyvinyl acetate (weight of water insoluble ammonium methacrylate copolymer: weight of polyvinyl acetate) in the melt-extruded pellet is in a range of 1:0.05 to 1:5 by weight.

2. The controlled release pharmaceutical composition according to claim 1, wherein the polyvinyl acetate is contained in a physical mixture with polypyrrolidone and wherein a mixing ratio of polyvinyl acetate and polypyrrolidone (weight of polyvinyl acetate:weight of polypyrrolidone) is in a range of 9.9:0.1 to 5:5 by weight.

3. The controlled release pharmaceutical composition according to claim 1, wherein a mixing ratio of the active ingredient and a polymer mixture of the water insoluble ammonium methacrylate copolymer and polyvinyl acetate (weight of active ingredient:weight of polymer mixture) in the melt-extruded pellet is in a range of 1:1 to 1:18 by weight.

4. The controlled release pharmaceutical composition according to claim 1, wherein the polymer coating layer is contained at 1% to 500% with respect to the weight of pellet.

5. The controlled release pharmaceutical composition according to claim 1, wherein the polymer coating layer further comprises at least one selected from the group consisting of plasticizer, lubricant, coloring agent, flavoring agent, sweetening agent, surfactant, stabilizer, antioxidant, foaming agent, paraffin, waxes, and anti-foaming agent.

6. The controlled release pharmaceutical composition according to claim 5, wherein the plasticizer is at least one selected from the group consisting of triethyl citrate, dibutyl phthalate, diethyl phthalate, dibutyl sebacate, diethyl sebacate, tributyl citrate, acetyl triethyl citrate, acetyl triethyl citrate, propylene glycol, triacetin, polyethylene glycols, cetyl alcohol, stearyl alcohol, and cetostearyl alcohol.

7. The controlled release pharmaceutical composition according to claim 5, wherein the lubricant is at least one selected from the group consisting of stearic acid, glyceryl behenate, glyceryl monostearate, magnesium stearate, calcium stearate, silica, talc, and magnesium silicate.

8. An oral formulation comprising a controlled release pharmaceutical composition according to claim 1.

9. The oral formulation of claim 8, wherein the oral formulation is in the form of capsule, plain tablet, double tablet, chewing tablet, rapid-disintegrable tablet, dry syrup formulation, syrup, jelly-type formulation, or granule.

10. The controlled release pharmaceutical composition according to claim 3, wherein the polyvinyl acetate is contained in a physical mixture with polypyrrolidone and wherein a mixing ratio of polyvinyl acetate and polypyrrolidone (weight of polyvinyl acetate:weight of polypyrrolidone) is in a range of 9.9:0.1 to 5:5 by weight.

11. The controlled release pharmaceutical composition according to claim 3, wherein the polymer coating layer is contained at 1% to 500% with respect to the weight of pellet.

12. The controlled release pharmaceutical composition according to claim 3, wherein the polymer coating layer further comprises at least one selected from the group consisting of plasticizer, lubricant, coloring agent, flavoring agent, sweetening agent, surfactant, stabilizer, antioxidant, foaming agent, paraffin, waxes, and anti-foaming agent.

13. The controlled release pharmaceutical composition according to claim 12, wherein the plasticizer is at least one selected from the group consisting of triethyl citrate, dibutyl phthalate, diethyl phthalate, dibutyl sebacate, diethyl sebacate, tributyl citrate, acetyl triethyl citrate, acetyl triethyl citrate, propylene glycol, triacetin, polyethylene glycols, cetyl alcohol, stearyl alcohol, and cetostearyl alcohol.

14. The controlled release pharmaceutical composition according to claim 12, wherein the lubricant is at least one selected from the group consisting of stearic acid, glyceryl behenate, glyceryl monostearate, magnesium stearate, calcium stearate, silica, talc, and magnesium silicate.

15. An oral formulation comprising a controlled release pharmaceutical composition according to claim 3.

16. The oral formulation of claim 15, wherein the oral formulation is in the form of capsule, plain tablet, double tablet, chewing tablet, rapid disintegrable tablet, dry syrup formulation, syrup, jelly-type formulation, or granule.

* * * * *